(12) United States Patent
Osborne et al.

(10) Patent No.: US 7,544,207 B2
(45) Date of Patent: Jun. 9, 2009

(54) MEDICAL DEVICE WITH BIOACTIVE AGENT

(75) Inventors: Thomas A. Osborne, Bloomington, IN (US); Jacob A. Flagle, Indianapolis, IN (US); Brian C. Case, Bloomington, IN (US); Joseph F. Obermiller, West Lafayette, IN (US); Ram H. Paul, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 176 days.

(21) Appl. No.: 11/244,991

(22) Filed: Oct. 6, 2005

(65) Prior Publication Data

US 2006/0136044 A1    Jun. 22, 2006

Related U.S. Application Data

(60) Provisional application No. 60/616,512, filed on Oct. 6, 2004.

(51) Int. Cl.
*A61F 2/24* (2006.01)
(52) U.S. Cl. .................................................. 623/2.16
(58) Field of Classification Search ................ 623/1.24, 623/1.42, 2.1–2.19, 916, 1.26, 1.4, 1.41, 623/2.42
See application file for complete search history.

(56) References Cited

U.S. PATENT DOCUMENTS 5,824,049 A * 10/1998 Ragheb et al. .............. 623/1.44
6,440,164 B1    8/2002 DiMatteo et al.
6,494,909 B2 * 12/2002 Greenhalgh ................ 623/1.24
6,508,833 B2    1/2003 Pavcnik et al.
2002/0099439 A1    7/2002 Schwartz et al.
2003/0083741 A1    5/2003 Woo et al.
2003/0181974 A1    9/2003 Xie et al.
2004/0047909 A1    3/2004 Ragheb et al.
2004/0059411 A1    3/2004 Strecker
2004/0093070 A1    5/2004 Hojeibane et al.
2004/0243219 A1    12/2004 Fischer et al.
2005/0163818 A1    7/2005 Sung et al.
2005/0187614 A1    8/2005 Agnew
2006/0282157 A1    12/2006 Hill et al.

FOREIGN PATENT DOCUMENTS

| WO | WO 01/54625 | * | 8/2001 |
| WO | WO 2004/080352 A1 | | 9/2004 |
| WO | WO 2004/082528 A2 | | 9/2004 |
| WO | WO 2004/082528 A3 | | 9/2004 |
| WO | WO 2005/082289 A1 | | 9/2005 |

* cited by examiner

*Primary Examiner*—David Isabella
*Assistant Examiner*—Suba Ganesan
(74) *Attorney, Agent, or Firm*—Buchanan Intellectual Property Office LLC

(57) ABSTRACT

Medical devices with one or more bioactive agents are provided for regulating fluid flow through a body vessel. Medical devices according to the invention can comprise prosthetic valves that include a bioactive agent.

5 Claims, 4 Drawing Sheets

MEDICAL DEVICE WITH BIOACTIVE AGENT

CROSS REFERENCE TO RELATED APPLICATION

This application claims priority to U.S. Provisional Application Ser. No. 60/616,512 filed on Oct. 6, 2004, the disclosure of which is hereby incorporated into this disclosure in its entirety.

FIELD

Medical devices that include one or more bioactive agents are disclosed. Particular embodiments of the medical devices are intraluminal valve prostheses that include one or more bioactive agents.

BACKGROUND

Medical devices are used in the treatment of a wide variety of conditions. Bioactive agents can be associated with medical devices to provide a device that includes a particular biological effect upon implantation in a host.

Many vessels in animal bodies transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction and close to prevent fluid flow in a reverse direction, i.e., retrograde flow. The valves can change from an open position in response to a variety of circumstances, including changes in the cross-sectional shape of the vessel and the fluid pressure within the vessel.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, which may lead to discomfort and possibly ulcers in the legs and ankles.

Current treatments for venous valve insufficiency include the use of compression stockings that are placed around the leg of a patient in an effort to force the vessel walls radially inward to restore valve function. Surgical techniques are also employed in which valves can be bypassed, eliminated, or replaced with autologous sections of veins having competent valves.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990s. Coronary and peripheral stents have been proven to provide a superior means of maintaining vessel patency, and have become widely accepted in the medical community. Furthermore, the use of stents has been extended to treat aneurysms and to provide occlusion devices, among other uses.

Recently, prosthetic valves that are implantable by minimally invasive techniques have been developed. Frequently, a graft member is attached to a support frame and provides a valve function to the device. For example, the graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, U.S. Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety. In other examples of prosthetic valves, a tube that terminates in leaflets is attached to one or more support frames to form a valve. The leaflets open to permit fluid flow in a first direction in response to fluid pressure on one side of the leaflets, and close to prevent fluid flow in a second, opposite direction in response to fluid pressure on opposite sides of the leaflets. An example of this configuration is provided in U.S. Pat. No. 6,494,909 to Greenhalgh for AN ENDOVASCULAR VALVE, which is hereby incorporated by reference in its entirety.

SUMMARY OF EXEMPLARY EMBODIMENTS

Medical devices that include one or more bioactive agents are disclosed. Particular embodiments of the invention relate to intraluminal valve prostheses that include one or more bioactive agents.

An intraluminal valve prostheses according to one exemplary embodiment comprises a graft member that comprises a bioactive agent.

Additional understanding of the invention can be obtained with review of the detailed description of exemplary embodiments, appearing below, and the appended drawings that illustrate various exemplary embodiments.

DETAILED DESCRIPTION OF EXEMPLARY EMBODIMENTS

The following provides a detailed description of exemplary embodiments. The description is not intended to limit the scope of the invention, or its protection, in any manner, but rather serves to enable those skilled in the art to practice the invention.

The invention provides medical devices that can be used in a variety of applications. For example, a medical device according to the invention can be used to provide intraluminal support to a body vessel. Medical devices according to exemplary embodiments comprise prosthetic valves that can be used to regulate fluid flow through a body vessel. The prosthetic valves can be implanted in a body vessel, or in any other suitable environment, to regulate the flow of fluid. Valves according to the invention can also be implanted in ducts, canals, and other passageways in the body, as well as cavities and other suitable locations. Valves according to exemplary embodiments of the invention can be implanted in the vessels of the vasculature, such as veins, to regulate the flow of blood through the vessels.

As used herein, the term "implanted," and grammatically related terms, refers to the positioning of an item in a particular environment, either temporarily, semi-permanently, or permanently. The term does not require a permanent fixation of an item in a particular position.

Figure 1:
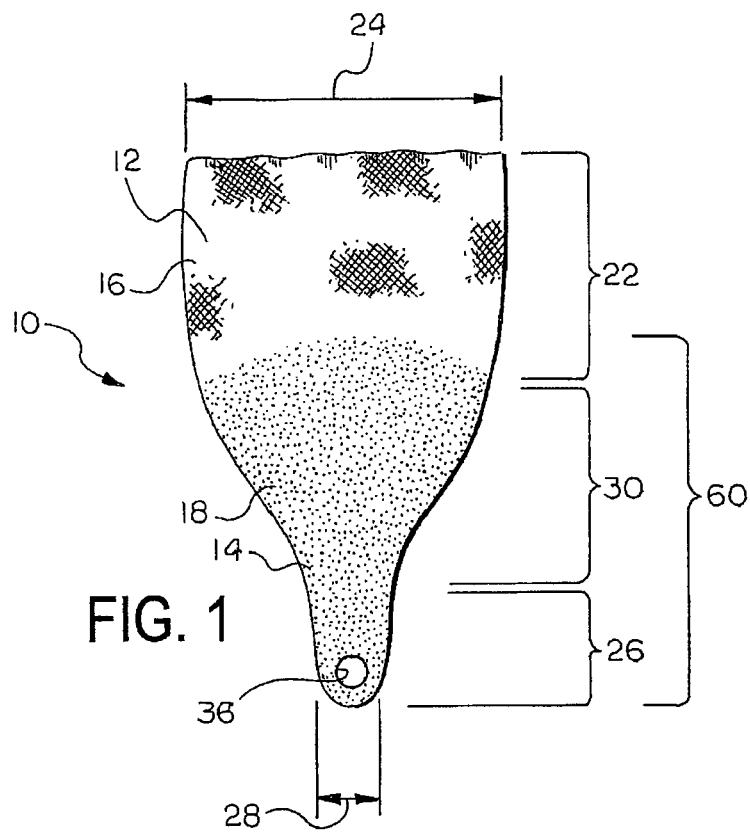
FIG. 1 is a perspective view of a medical device according to a first exemplary embodiment.
Figure 2:
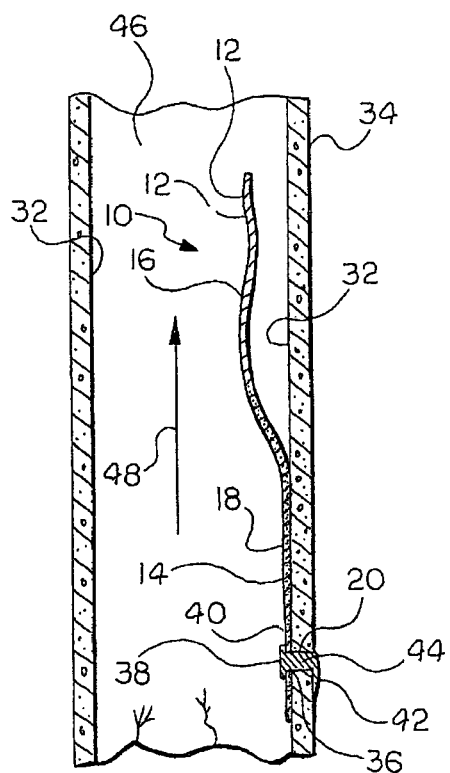
FIG. 2 is a sectional view of a body vessel containing the medical device illustrated in FIG. 1.
Figure 3:
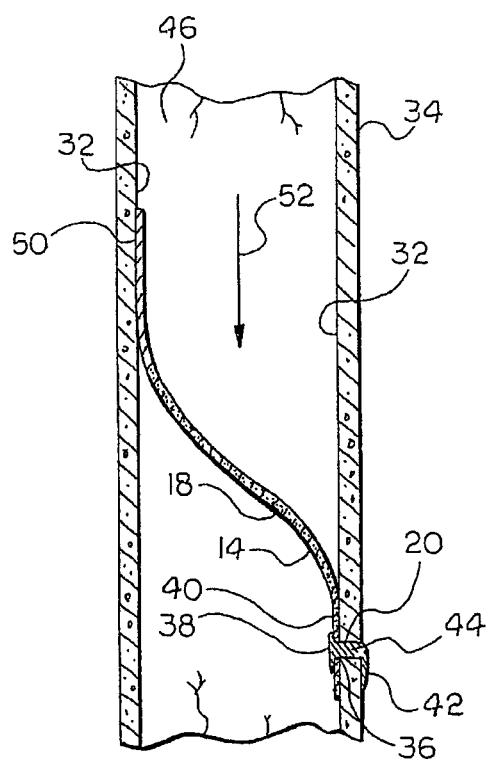
FIG. 3 is a sectional view of a body vessel containing the medical device illustrated in FIG. 1.

FIGS. 1 through 3 illustrate a first exemplary embodiment. The medical device of this embodiment is a prosthetic valve 10 that can be used to regulate the flow of fluid through a body vessel. The valve 10 includes a graft member 12, which can also be referred to as a leaflet, that has a base portion 14 and a valve portion 16. The valve 10 also includes a means for maintaining an axial position of a portion of the leaflet 12 in a body vessel in which the valve 10 is implanted. A bioactive agent 18 is associated with the prosthetic valve 10. As used herein, the phrase "associated with" refers to a spatial relationship between two items, such as a graft member and a bioactive agent. The phrase encompasses a spatial relationship in which one item is disposed on a surface of another, as well as a spatial relationship in which one item is disposed in a portion of another. Accordingly, in medical devices according to the invention, a bioactive agent can be disposed on a portion of the device, disposed within a portion of the device, or associated with the device in any other suitable manner.

Any suitable structure can be used as the means for maintaining an axial position of the leaflet 12 in a body vessel, and exemplary structure is illustrated in FIGS. 1 through 3. The specific structure chosen for any particular valve according to the invention will depend on several considerations, including the nature of the leaflet and the vessel in which the valve will be implanted. The structure need only be able to substantially maintain a position of a portion of the leaflet on an axis of a vessel in which the leaflet is implanted while fluid flows through the vessel. Examples of suitable structures for the means for maintaining an axial position include barbs, integrally formed anchors, support frames, and their equivalents. In the embodiment illustrated in FIGS. 1 through 3, the means for maintaining an axial position comprise a barb 20 that is structurally distinct from the leaflet 12.

The leaflet 12 comprises a section of material. The leaflet 12 can be formed of any suitable material, and need only be biocompatible or be able to be made biocompatible and be able to perform as described herein. The leaflet 12 advantageously can be formed of a flexible material. Examples of suitable materials for the leaflet 12 include natural materials, synthetic materials, and combinations of natural and synthetic materials. Examples of suitable natural materials include extracellular matrix (ECM) materials, such as small intestine submucosa (SIS), and other bioremodellable materials, such as bovine pericardium. Other examples of ECM materials that can be used in the medical devices of the invention include stomach submucosa, liver basement membrane, urinary bladder submucosa, tissue mucosa, and dura mater. Examples of suitable synthetic materials include polymeric materials, such as expanded polytetrafluoroethylene and polyurethane. ECM materials are particularly well-suited materials for use in the leaflet 12 at least because of their abilities to remodel and to provide a scaffold onto which cellular in-growth can occur, eventually allowing the material to remodel into a structure of host cells. Resorbable materials, such as polyglycolic acid, polylactic acid, polycaprolactone and other suitable resorbable materials can also be used, including the resorbable materials listed below.

The leaflet 12 can have any suitable size and configuration, and the specific size and configuration chosen for the leaflet in a particular valve according to the invention will depend on several considerations, including the size, configuration, and/or nature of the vessel in which the valve will be implanted. In the embodiment illustrated in FIGS. 1 through 3, the leaflet 12 includes a first portion 22 having a first width 24, and a second portion 26 having a second width 28. The first width 24 is greater than the second width 28. Advantageously, the first portion 22 includes the valve portion 16. Also advantageously, the second portion 26 includes the base portion 14. In the illustrated embodiment, a transition region 30 is disposed between the first 22 and second 26 portions, and includes a width that tapers from the first width 24 to the second width 28.

As best illustrated in FIGS. 2 and 3, the base portion 14 provides a portion of the leaflet 12 that can be anchored to a wall 32 of a body vessel 34 in which the valve 10 is implanted. When the valve 10 is implanted in a body vessel, the base portion 14 remains substantially static, even as fluid flows through the body vessel 34, because the base portion 14 is associated with a means for maintaining an axial position of a portion of the leaflet 12 in the body vessel. For example, in the illustrated embodiment, the base portion 14 defines an opening 36. Barb 20 is partially disposed in the opening 36, with a head 38 disposed adjacent one surface 40 of the leaflet 12. An anchor portion 42 of the barb 20 is disposed external to the body vessel 34, and a body portion 44 of the barb 20 is disposed within the opening 36 and through the wall 32 of the body vessel 34. The head 38 and anchor portion 42 of the barb 20 can be compressed toward each other during implantation of the valve 10.

The barb 20 can be formed of any suitable material, and need only be biocompatible or able to be made biocompatible. Also, the barb 20 can have any suitable size and configuration, and the specific size and configuration chosen for any particular valve according to the invention will depend on several considerations, including the nature of the vessel in which the valve is being implanted. Also, the specific material used for the barb 20 can depend on the material used for the leaflet 12. For example, in embodiments in which the leaflet 12 comprises a bioremodellable material, such as SIS, the barb 20 can be formed of a resorbable material. As used herein, the term "resorbable" refers to the ability of a material to be absorbed into a tissue and/or body fluid upon contact with the tissue and/or body fluid. The contact can be prolonged, and can be intermittent in nature. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), and polyglycolide; trimethlyene carbonate; polycaprolactone; poly-beta hydroxy acids such as polyhydroxybutyrate and polyhydroxyvalerate; and other polymers such as polyphosphazines, polyorganophosphazines, polyanhydrides, polyesteramides, polyorthoesters, polyethylene oxide, polyester-ethers (e.g., polydioxanone) and polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

In embodiments in which the barb, or another suitable means for maintaining an axial position of the leaflet, comprises a resorbable material, the base portion 14 of the leaflet 12, or a portion thereof, can eventually become incorporated into the wall 32 of the body vessel 34, providing the desired anchoring function. Once the base portion 14 is sufficiently incorporated into the vessel wall 32, additional anchoring, such as that provided by the barb 20, may no longer be needed. If the barb 20 is formed of a resorbable material, the barb 20 would be eliminated gradually as the material of the barb 20 is absorbed, allowing the incorporated base portion 14 to perform the anchoring function.

The prosthetic valve 10 of this exemplary embodiment does not have a support frame, an optional element that may or may not be desirable in a particular embodiment.

As best illustrated in FIGS. 2 and 3, the valve portion 16 is moveable between first and second positions when the valve 10 is implanted in a body vessel 34. In the first position, illustrated in FIG. 2, the valve portion 16 is positioned within the body vessel 34 so that an opening 46 is formed between the vessel wall 32 and the valve portion 16. Fluid is able to flow through the body vessel 34 at the position of the valve 10 via the opening 46 in a first direction, represented by arrow 48. As such, the leaflet 12 can be referred to as being in an open configuration and as permitting fluid flow through the body vessel 34 in the first direction 48.

In the second position, illustrated in FIG. 3, a surface 50 of the valve portion 16 is disposed adjacent a portion of the wall 32 of the body vessel 34. In this configuration, the opening 46 of the first position, described above, is substantially eliminated. Accordingly, the leaflet 12 substantially prevents fluid flow through the body vessel 34 in a second, opposite direction, represented by arrow 52. As such, the leaflet 12 can be referred to as being in a closed configuration.

The valve portion 16 can move between the first and second positions, i.e., between open and closed configurations, in response to a change in the direction of fluid flow through a body vessel in which the valve 10 is implanted, such as a change from flow in the first direction 48 to a flow in the second, opposite direction 52. Also, the valve portion 16 can move between the first and second positions in response to a change in fluid pressure on one or more sides of the leaflet 12.

In the embodiment illustrated in FIGS. 1 through 3, the bioactive agent 18 is disposed on the leaflet 12. As best illustrated in FIGS. 2 and 3, the bioactive agent 18 can be disposed within a thickness of the leaflet 12.

Any suitable bioactive agent can be used in the invention, and the specific bioactive agent, or bioactive agents, selected for any particular medical device according to the invention will depend upon several considerations, including the desired effect and the type of treatment and/or procedure in which the medical device is being used. Examples of suitable bioactives include heparin, covalent heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; paclitaxel; tamoxifen citrate, Taxol® or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin, sirolimus, or another immunosuppressive agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; $^{60}$Co, $^{192}$Ir, $^{32}$P, $^{111}$In, $^{90}$Y, $^{99m}$Tc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine betahydroxylase conjugated to saporin or other antibody target therapy agents; enalapril or other prodrugs; any endothelium progenitor cell attracting, binding and/or differentiating agents, including suitable chemoattractive agents and suitable polyclonal and monoclonal antibodies; cell migration inhibiting agents, such as smooth muscle cell migration inhibitors, such as Bamimistat, prolylhydrolase inhibitors, Probacol, c-proteinase inhibitors, halofuginone, and other suitable migration inhibitors; and gene therapy agents, or a mixture of any of these.

The bioactive agent 18 is disposed on a portion 60 of the leaflet 12. The portion 60 can be any suitable portion of the leaflet 12. Advantageously, the portion 60 is a portion of the leaflet 12 for which it is desirable to have the effect that the bioactive agent 18 is able to achieve within a biological system. For example, the prosthetic valve 10 illustrated in FIGS. 1 through 3 functions by moving between open and closed positions. As illustrated in FIGS. 2 and 3, portions of the leaflet 12 makes contact with the vessel wall 32 during such movement. If the leaflet 12 comprises a material that may become temporarily or permanently adhered to or otherwise attached to the vessel wall 32 as a result of such contact, it may be desirable to protect one or more portions of the leaflet 12 during contact. A bioactive agent 18 that prevents cellular deposition, ingrowth, or proliferation can be placed on one or more portions of the leaflet 12 to achieve such protection. An antiproliferative bioactive agent, such as paclitaxel, is believed to be advantageous in this regard.

The use of a bioactive agent 18 to protect a portion of a valve leaflet 18 is particularly advantageous for leaflets that comprise a bioreodellable material. In these embodiments, the bioactive agent 18 protects a portion of the leaflet 18 while another portion begins the remodeling process. The protected portion 60 will begin the remodeling process as the bioactive agent 18 dissipates from the leaflet 18. This may allow for selective protection and remodeling during a critical period, such as a period following implantation.

In the embodiment illustrated in FIGS. 1 through 3, the portion 60 that includes the bioactive agent 18 is a portion that may contact the vessel wall 32 during valve function, such as base portion 14. It is understood that the bioactive agent 18 can be disposed on one or more portions of a medical device without departing from the scope of the invention.

Figure 4:
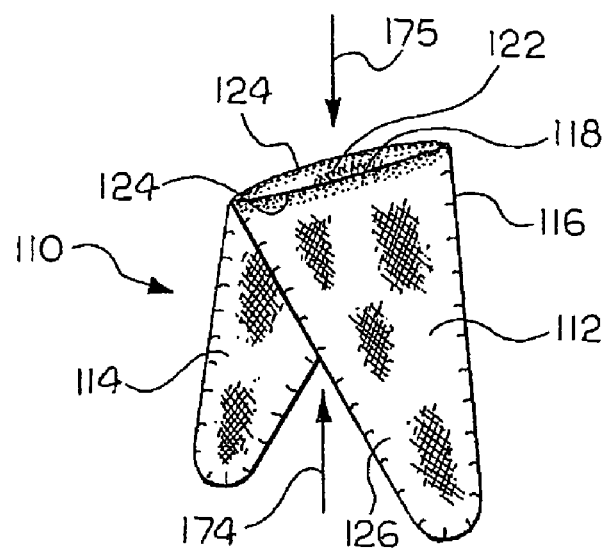
FIG. 4 is a perspective view of a medical device according to a second exemplary embodiment.
Figure 5:
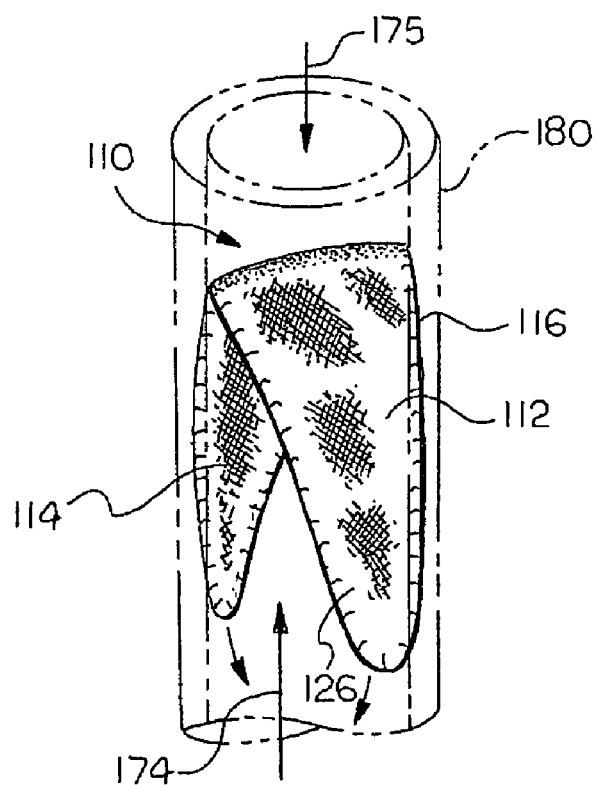
FIG. 5 is a perspective view of the medical device illustrated in FIG. 4 disposed within in a body vessel.

FIGS. 4 and 5 illustrate a second exemplary embodiment. The medical device according to this embodiment is a prosthetic valve 110 for regulating fluid flow through a body vessel. The valve 110 includes two leaflets 112, 114 that are attached to a support frame 116. Each leaflet 112, 114 has a free edge 118, 120 that is not attached to the support frame 116. The free edges 118, 120 cooperatively define valve orifice 122. The leaflets 112, 114 are both movable between first and second positions. In the first position, illustrated in FIG. 7, the orifice 122 is open and allows fluid flow through the valve 110 in a first direction, represented by arrow 174. In the second position, the free edges 118, 120 of leaflets 112, 114 come together to close the orifice 122 and substantially prevent fluid flow through the valve 110 in a second, opposite direction, represented by arrow 175.

In this embodiment, a bioactive agent 124 is associated with each leaflet 112, 114 adjacent the free edge 118, 120. Thus, the bioactive agent 124 is positioned adjacent the valve orifice 122. A bioactive agent 124 positioned in this manner may confer a desired effect onto the leaflets 112, 114 adjacent the valve orifice 122. An anitproliferative agent, such as paclitaxel, may be used in this manner to delay remodeling of the free edges 118, 120 of leaflets 112, 114 formed of a remodelable material. Leaflets 112, 114 with a bioactive agent positioned in this manner are expected to remodel at portions lacking the agent 124 first, such as base portion 126, which may improve anchoring of the valve 110.

FIG. 5 illustrates the prosthetic valve 110 disposed within a body vessel 180. The valve 110 is shown in a closed configuration.

Figure 6:
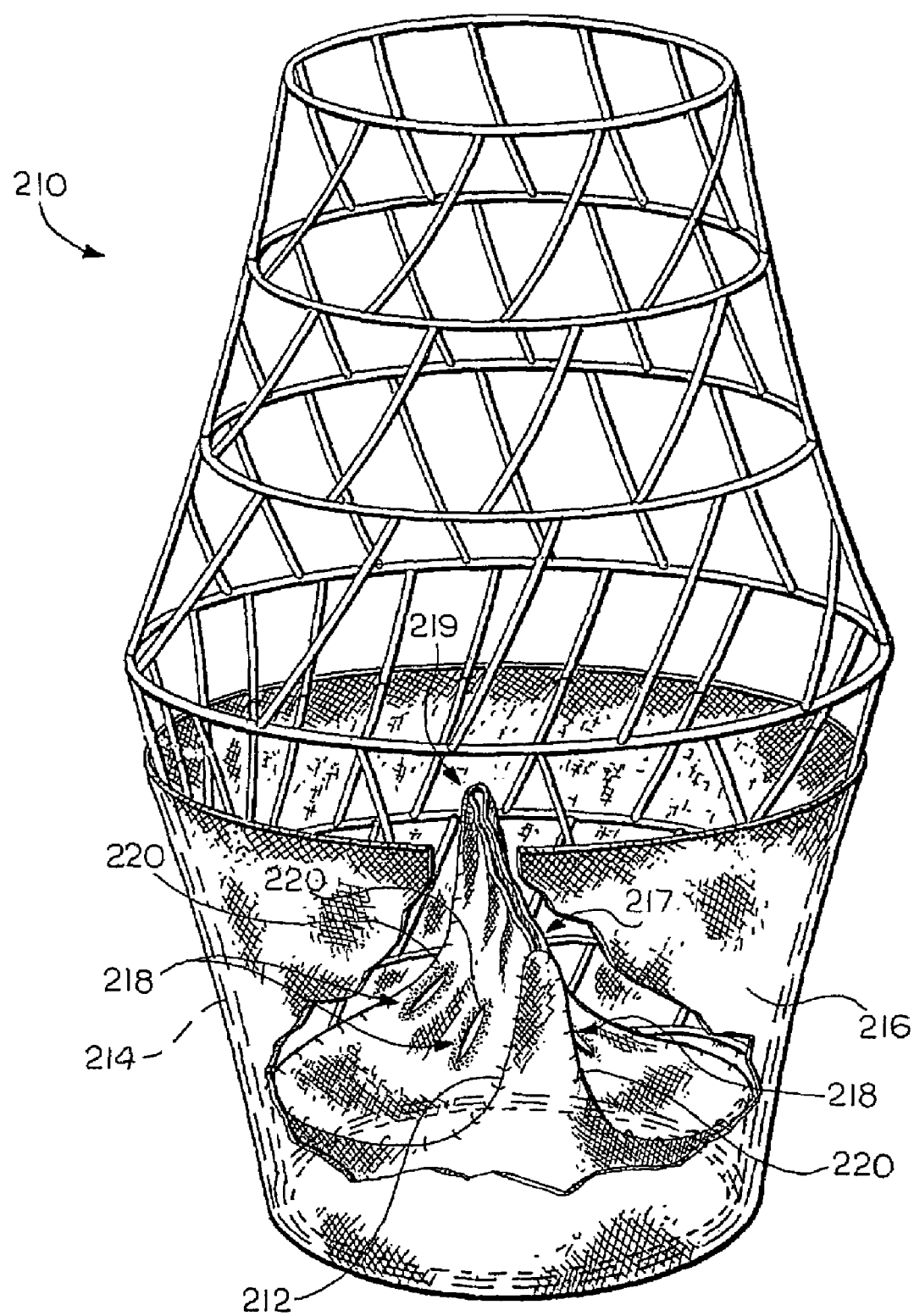
FIG. 6 is a perspective view of a medical device according to a third exemplary embodiment.

FIG. 6 illustrates a third exemplary embodiment. The medical device according to this embodiment is a prosthetic valve 210 for regulating fluid flow through a body vessel. The prosthetic valve 210 comprises a first tubular frame member 212 and a second tubular frame member 214 disposed circumferentially around the first tubular frame member 212. A tubular graft member 216 is disposed about a portion of the first tubular frame member 212 and into a space between the frame members 212, 214. Opposing sides of one end 217 of the graft member 216 collapse onto the first tubular member 212 to close an opening 219 defined by the end of the graft member 216 and provide a valving function.

In this embodiment, the graft member 216 defines a plurality of openings 218. The slits allow a controlled amount of retrograde flow through the valve 210 when the graft member 216 is in a closed configuration, as illustrated. This allowance of retrograde flow provides a beneficial flushing effect in the valve pocket, which may avoid pooling of fluid in the valve pocket. A bioactive agent 220 is associated with the graft member 216 adjacent the opening 218. This positioning of the bioactive agent can provide a desired effect near the opening 218, such as a delay in remodeling of a leaflet formed of a remodel able material, as described above.

It is understood that any suitable number, size, configuration, and positioning of openings 218 in the graft member 216 can be used.

Figure 7:
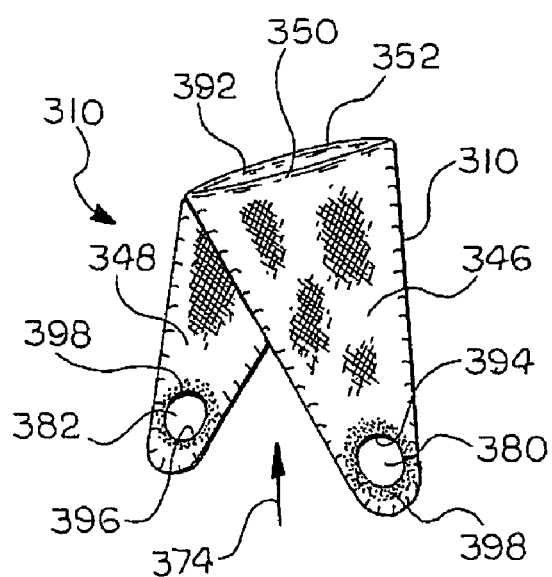
FIG. 7 is a perspective view of a medical device according to a fourth exemplary embodiment.

FIG. 7 illustrates a fourth exemplary embodiment. The medical device according to this embodiment comprises a prosthetic valve 310. The valve 310 includes two leaflets 346, 348 that are attached to a support frame 310. Each leaflet 346, 348 has a free edge 350, 352 that is not attached to the support frame 310. The free edges 350, 352 cooperatively define valve orifice 392. The leaflets 346, 348 are both movable between first and second positions. In the first position, illustrated in FIG. 7, the orifice 392 is open and allows fluid flow through the valve 310 in a first direction, represented by arrow 374. In the second position, the free edges 350, 352 of leaflets 346, 348 come together to close the orifice 392 and substantially prevent fluid flow through the device in a second, opposite direction. Each leaflet 346, 348 defines an opening 380, 382 that allows a controlled amount of retrograde flow to pass through the medical device 300 when the valve orifice 392 is closed. In this embodiment, each of the openings 380, 382 is defined entirely by the respective leaflet 346, 348. Thus, one or more edges 394, 396 of the leaflets 346, 348 define each of the openings 380, 382. A bioactive agent 398 is associated with each leaflet 346, 348 adjacent the respective opening 380, 382.

Figure 8:
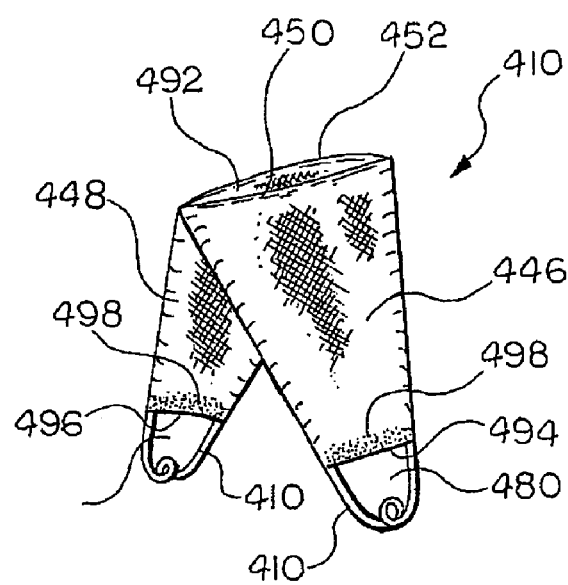
FIG. 8 is a perspective view of a medical device according to a fifth exemplary embodiment.

FIG. 8 illustrates a fifth exemplary embodiment. The medical device according to this embodiment comprises a prosthetic valve 410. The prosthetic valve 410 of this embodiment is similar to the device illustrated in FIG. 7, except that each opening 480, 482 is partially defined by an edge 494, 496 of a leaflet 446, 448 and a portion of the support frame 410. This configuration of the openings 480, 482 may be advantageous if the valve leaflets 446, 448 are formed of a bioremodellable material or other material that can become adhered to or incorporated into a vessel wall following repeated and/or prolonged contact between the valve leaflets 446, 448 and the vessel wall. Similar to the embodiment illustrated in FIG. 7, free edges 450, 452 of leaflets 446, 448 define valve orifice 492 which opens and closes to regulate fluid flow through the device 400. A bioactive agent 498 is associated wit each leaflet 446, 448 at the respective free edge 450, 452 that partially defines the respective opening 480, 482.

Figure 9:
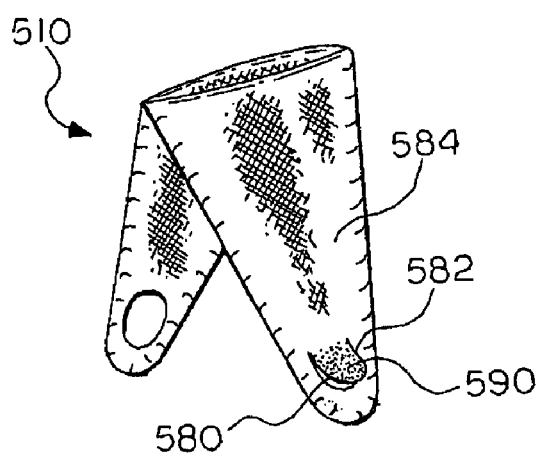
FIG. 9 is a perspective view of a medical device according to a sixth exemplary embodiment.

FIG. 9 illustrates a sixth exemplary embodiment. The medical device according to this embodiment comprises a prosthetic valve 510. The prosthetic valve 510 is similar to the valve 310 illustrated in FIG. 7, except that the opening 580 that allows retrograde flow is defined by a flap 582 in the leaflet 584. A flap configuration may allow retrograde flow to proceed through the opening, and minimize or prevent any antegrade flow from proceeding through the opening. As used herein, the term "flap" refers to a section of material that is connected to or integrally formed with adjacent material at one side or end, but is free of adjacent material at another side or end. The flap is a moveable section of material that is adjacent the opening. As the flap moves, it is able to temporarily and substantially close the opening. Specific examples of suitable shapes for the flap 582 include a partial square flap, a partial triangular flap, a partial ovoid flap, and a partial teardrop-shaped flap. The actual shape chosen for the flap will depend on various factors, including the desired quantity of retrograde flow, the size and configuration of the leaflet(s) of the medical device, the desired ability of the flap to close, and the size and configuration of the vessel in which the medical device will be employed. An optional support, such as a suture that traverses the opening 580, can be added to prevent the flap 582 from inverting into the opening 580.

A bioactive agent 590 is associated with the flap 582. This positioning of the bioactive agent 590 may provide a desired effect at the flap 582, such as a delay in remodeling as described above. Such a delay may be particularly desirable in embodiments that include a flap because it may allow the flap to open and close until the remainder of the leaflet has started or completed remodeling. Once the bioactive agent 590 has dissipated, the flap can remodel, which me result in permanent closure of the flap due to adherence to the remainder of the leaflet.

Figure 10:
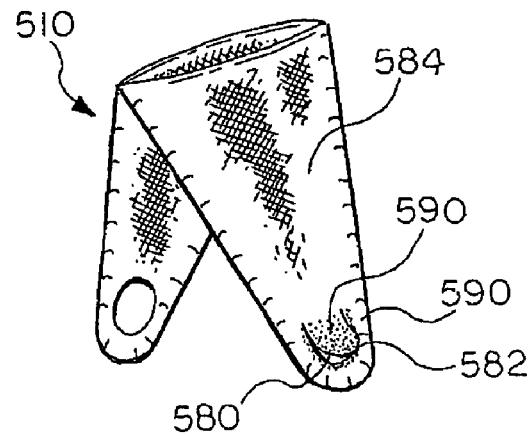
FIG. 10 is a perspective view of a medical device according to a seventh exemplary embodiment.

FIG. 10 illustrates an alternative configuration of the embodiment illustrated in FIG. 9. As illustrated in FIG. 10, the bioactive agent 590 also can be associated with the portion of the leaflet 584 that defines the opening 580 underlying the flap 582. This positioning of the bioactive agent 590 may enhance the desired effect, such as a delay in remodeling near the opening 580.

The foregoing detailed description provides exemplary embodiments of the invention and includes the best mode for practicing the invention. These embodiments are intended only to serve as examples of the invention, and not to limit the scope of the invention, or its protection, in any manner.

We claim:

1. A prosthetic valve for selectively permitting fluid flow through a body vessel in a first direction and substantially preventing fluid flow through said body vessel in a second, opposite direction, said prosthetic valve comprising:
   a support frame having radially expanded and radially compressed configurations;
   a first bioremodellable leaflet attached to the support frame and including a first base portion attached to the support frame and a first free edge that is moveable within said body vessel;
   a second bioremodellable leaflet attached to the support frame and including a second base portion attached to the support frame and a second free edge that is moveable within said body vessel; and
   an antiproliferative agent associated with at least one of the first and second free edges;
   wherein the first and second free edges cooperatively define a valve orifice that opens and closes in response to movement of the first and second free edges; and
   wherein the first and second base portions are free of the antiproliferative agent such that remodelling of the at least one free edge with which the antiproliferative agent is associated is delayed with respect to remodelling of the first and second base portions.

2. The prosthetic valve according to claim 1, wherein at least one of the first and second leaflets comprises an edge that at least partially defines an opening for permitting a controlled amount of said fluid flow through said body vessel in said second, opposite direction.

3. The prosthetic valve according to claim 2, wherein the at least one of the first and second leaflets defines a flap capable of substantially covering the opening.

4. The prosthetic valve according to claim 1, wherein the first and second leaflets comprise an extracellular matrix material.

5. The prosthetic valve according to claim 1, wherein the first and second leaflets comprise small intestine submucosa.

* * * * *